United States Patent [19]

Clifford

[11] 4,331,669
[45] May 25, 1982

[54] FUNGICIDAL PYRIDYL ARYLUREAS, COMPOSITIONS CONTAINING THEM AND METHOD OF CONTROLLING FUNGI AND BACTERIA

[75] Inventor: David P. Clifford, Kings Lynn, England

[73] Assignee: Dow Chemical Company Limited, England, England

[21] Appl. No.: 160,405

[22] Filed: Jun. 17, 1980

[30] Foreign Application Priority Data

Feb. 5, 1980 [GB] United Kingdom ................. 8003828

[51] Int. Cl.³ .................... A01N 43/40; C07D 213/75
[52] U.S. Cl. .................................... 424/263; 546/305; 546/306; 546/309
[58] Field of Search ................. 546/305, 306; 424/263

[56] References Cited

U.S. PATENT DOCUMENTS

| | | | |
|---|---|---|---|
| 2,050,557 | 8/1933 | Bockmühl et al. | 546/305 |
| 3,404,152 | 10/1968 | Thiele et al. | 546/306 |
| 3,426,031 | 2/1969 | Fischback | 424/263 |
| 4,001,256 | 1/1977 | Callahan et al. | 546/306 |
| 4,048,333 | 9/1977 | Galabov et al. | 424/322 |
| 4,088,766 | 5/1978 | Callahan et al. | 424/263 |
| 4,112,100 | 9/1978 | Callahan et al. | 424/263 |
| 4,193,788 | 3/1980 | Shudo et al. | 546/305 |
| 4,203,988 | 5/1980 | Bolhofer et al. | 546/306 |
| 4,279,639 | 7/1981 | Okamoto et al. | 546/306 |

Primary Examiner—John M. Ford
Assistant Examiner—Natalia Harkaway
Attorney, Agent, or Firm—S. Preston Jones; Ronald G. Brookens

[57] ABSTRACT

A compound having the formula

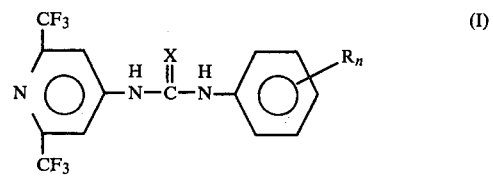

wherein R is halogen, trichloromethyl, trifluoromethyl, nitro, cyano, $C_1$–$C_4$ alkyl or $C_1$–$C_4$ alkoxy; X is NH, O or S and n is an integer of from 1 to 5, which is useful as a fungicide on plants and other substrates susceptible to fungicidal attack.

14 Claims, No Drawings

FUNGICIDAL PYRIDYL ARYLUREAS, COMPOSITIONS CONTAINING THEM AND METHOD OF CONTROLLING FUNGI AND BACTERIA

SUMMARY OF THE INVENTION

This invention relates to novel pyridyl arylureas corresponding to the formula

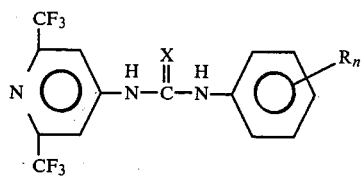

wherein R is halogen, trichloromethyl, trifluoromethyl, nitro, cyano, $C_1$–$C_4$ alkyl or $C_1$–$C_4$ alkoxy; X is NH, O or S and n is an integer of from 1 to 5; and to fungicidal and bactericidal compositions containing such compounds, to methods for producing such compounds and to a method of controlling fungi and bacteria with such compounds.

The novel compounds of the present invention are liquids or crystalline solid materials which are somewhat soluble in many common organic solvents and of very low solubility in water. These compounds exhibit strong fungicidal and bactericidal properties.

The preferred compounds are those having the formula I, in which R is 4$CF_3$; 3,4-$Cl_2$; 3-$CF_3$, 4-Cl; 3,4,5-$Cl_3$; 3-$CF_3$; 4-Cl, 4-$OCH_3$; and X=O or S.

The present invention also provides a process for the preparation of pyridyl arylureas of formula I in which a pyridinylisocyanate or isothiocyanate of the general formula

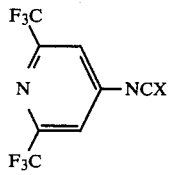

in which X=O or S, is reacted with an aniline of the general formula

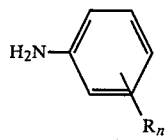

wherein R and n are as hereinabove set forth, in the presence of an inert diluent or solvent.

The present reaction scheme can be represented by the following equation

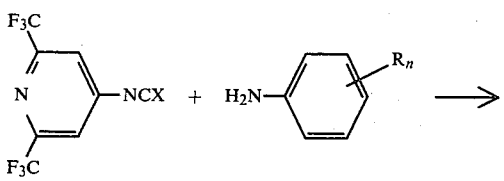

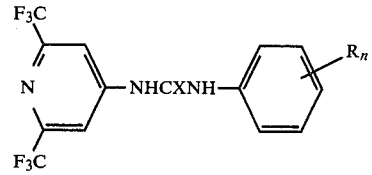

The compounds of the formula II can be prepared by the following course of reaction starting with the reaction of 2,6-lutidine and chlorine with the elimination of hydrogen chloride to yield 4-chloro-2,6-bis(trichloromethyl)pyridine (IV). The reaction is carried out in the vapor phase in the presence of a suitable diluent especially carbon tetrachloride and an inert atmosphere preferentially nitrogen. The reaction temperature can be varied within a fairly wide range. In general, the reaction is carried out between 350° and 600° C. preferably between 450° and 550° C.

In carrying out the process, the amounts of the reactants are not critical, some of the desired product compound being obtained when employing the reactants in almost any amounts. However, the reaction consumes the reactants in proportions representing a molar ratio of 7:1 chlorine:2,6-lutidine and the use of amounts which represents such proportions is preferred.

The resulting product (IV), may be fluorinated by treatment with an appropriate inorganic fluoride (V), to give the fluorinated material (VI), according to the following reaction sequence

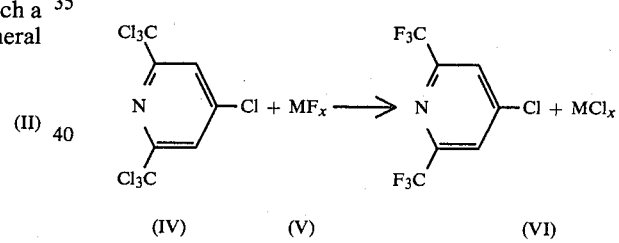

in which M=Hydrogen and x=1 or M=Antimony and x=3.

In the above reaction sequence, it is preferred that in the $MF_x$ reactant, M=Antimony and x=3. Chlorine is also present in essentially equimolar amounts to catalyse the reaction. The reaction temperatures can be varied within a fairly wide range. In general, the reaction is carried out at between 80° and 130° C., preferably 95°–110° C. The amounts of reactants to be employed are not critical, some of the desired product being obtained when employing the reactants in almost any amounts. However, the reaction consumes the reactants in a molar ratio of 4-chloro-2,6-bis(trichloromethyl)-pyridine (IV),:antimony trifluoride:chlorine of 1:2:2 and the use of amounts which represent such proportions is preferred. The product can be separated by conventional procedures but it is preferred to separate by steam distillation. The 4-chloro-3,5-bis-trifluoromethylpyridine (VI) so formed, may be aminated to give 4-amino-2,6-bis(trifluoromethyl)pyridine (VII) by reaction with aqueous or anhydrous ammonia. The course of the reaction can be represented by the following equation:

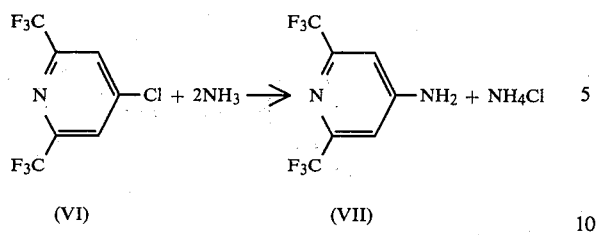

(VI)          (VII)

in which the aminated material (VII), is formed with elimination of hydrogen chloride which is conveniently scavenged by ammonia.

Thus, compounds of formula II may be prepared by the treatment of 4-amino-3,5-bis(trifluoromethyl)pyridine (VII), with oxalyl chloride or thiophosgene the reaction being carried out preferably in the temperature range +50° and 150° C. The former results in the formation of the desired starting product of the formula II, where X=O, with the elimination of hydrogen chloride and carbon monoxide and the latter in the formation of the product of formula II, where X=S, with the elimination of hydrogen chloride. The amines listed are compounds generally known to those skilled in the art and which can be prepared according to the methods which are generally known and customary in the laboratory.

Diluents which can be used for the reaction of the products of formula II with those of formula III, are those organic solvents which are inert to isocyanates and isothiocyanates, especially dry hydrocarbons, for example, ligroin, petroleum ether (Pet) in the boiling range between 40° and 150° C., benzene, toluene, chloro and dichlorobenzenes, chlorinated hydrocarbons such as carbon tetrachloride, ketones such as acetone, acetonitrile and dimethylformamide.

The reaction temperature can be varied over a fairly wide range −20° and 100° C. for isocyanates and 50° and 100° C. for isothiocyanates.

The amounts of the reactants to be employed are not critical, some of the desired product compound being obtained when employing the reactants in any amounts. However, the reaction consumes the reactants in amounts representing equimolar proportions, and the use of amounts which represent such proportions is preferred.

In carrying out the reaction, the reactants can be contacted together in any convenient fashion and maintained for a period of time in the desired reaction temperature range until the reaction is complete. Following the completion of the reaction, the reaction mixture can be employed as such. However, the desired product compound can be separated from the reaction mixture by conventional procedures. Most typically, the reaction mixture is dried and filtered and the organic liquid employed as reaction medium can be removed from the filtrate by evaporation under subatmospheric pressure. The product so obtained can be used without purification or can be purified by conventional procedures. For example, the separated product can be mixed with a quantity of any of the organic liquids to be employed as reaction medium, the resulting mixture filtered to separate insoluble by-product materials, and the organic liquid removed from the filtered mixture by evaporation under subatmospheric pressure, to obtain the purified product. Also, in the instance of those products which are solids the separated product can be purified by recrystallization from a solvent such as one of those listed herein above as diluents.

DESCRIPTION OF SOME PREFERRED EMBODIMENTS

The following examples serve to illustrate the practice of the present invention but are not intended to be limitations upon the overall scope of the same. The percentages (%) as set forth in the examples are weight percentages.

EXAMPLE 1

Preparation of 4-chloro-2,6-bis-trichloromethylpyridine

A gaseous mixture comprising 2,6-lutidine (2–3%), chlorine (30–40%) and a mixture of nitrogen and carbon tetrachloride as a diluent (ca. 60%) were passed through a tubular reactor (12″×1″) at 450°–550° C. in 2 seconds. The vapors were cooled and the title compound isolated in good yield, m.p. 101°–102° C.

EXAMPLE 2

Preparation of 4-chloro-2,6-bis(trifluoromethyl)pyridine

To a stirred mixture of 4-chloro-2,6-bis-trichloromethylpyridine (104.5 grams (g), 0.3 mole) and anhydrous antimony trifluoride (126.3 g, 0.7 mole) was introduced an atmosphere of chlorine. The ensuing exotherm was controlled by adjusting the rate of influx of chlorine gas and a temperature of 100°–110° C. maintained. On completion of the reaction, the temperature was allowed to fall to 50° C. and the mixture added to ice cold hydrochloric acid (650 ml, 8%). The mixture was steam distilled and the filtrate extracted with methylene chloride. The solvent was removed under reduced pressure from the dried solution (MgSO$_4$) to give the title compound in a yield of 52.7 g, 70% of theoretical. The product had a melting point (m.p.) of 57°–60° C.

EXAMPLE 3

Preparation of 4-amino-2,6-bis(trifluoromethyl)pyridine (a) A mixture of 4-chloro-2,6-bis(trifluoromethyl)pyridine (50 g, 0.20 mole) in concentrated ammonia (250 ml, density 0.88) and ethanol (250 ml) containing copper sulphate (ca. 0.5 g) was stirred and heated in a pressure vessel at 100°–120° C. for 5 hours. The mixture was cooled, extracted with methylene chloride and dried over MgSO$_4$. The solvent was removed under reduced pressure leaving the title compound as a cream solid. The product was recovered in a yield of 26 g, (56% of theoretical), m.p. 147°–149° C.

Crystallization from carbon tetrachloride gave a colorless (Col) solid, m.p. 146.5°–147° C.

C$_7$H$_4$F$_6$N$_2$: Found, C, 36.48; H, 1.87; N, 12.15. Required (Req.), C, 36.52; H, 1.74; N, 12.17%.

(b) 4-Chloro-2,6-bis(trifluoromethyl)pyridine (51 g) and anhydrous ammonia (124 ml) were heated in a pressure vessel at 100° C. for 2 hours. The ammonia was evaporated off and the pale yellow solid remaining was extracted with acetone, concentrated, and added to ice water. The solid thus formed was filtered, dried in vacuo at 65° C. to give the title compound in a yield of 41.5 g, 90% of theoretical, m.p. 146.5°–147° C.

EXAMPLE 4

Preparation of 4-Isocyanato-2,6-bis(trifluoromethyl)pyridine

To a stirred and refluxing solution of oxalyl chloride (64 g, 0.5 mole) in dry benzene (100 ml) was added a slurry of 4-amino-2,6-bis(trifluoromethyl)pyridine (20 g, 0.087 mole) in warm benzene (150 ml) over 1 hour. The mixture was then heated under gentle reflux for 5 hours, cooled and filtered. The solvent and excess oxalyl chloride were removed from the filtrate and the oil taken up in dry dichlorobenzene (100 ml) and heated under gentle reflux for 12 hours. The solvent was removed at 90° C./20 mm Hg leaving the titled isocyanate in good yield.

EXAMPLE 5

Preparation of 4-Isothiocyanato-2,6-bis(trifluoromethyl)pyridine

4-Amino-2,6-bis(trifluoromethyl)pyridine (10 g, 0.043 mole) and thiophosgene (21.9 g, 0.18 mole) in dry benzene (250 ml) containing triethylamine (6 drops) were heated under reflux for 5 hours. The solvent and excess thiophosgene were removed under reduced pressure to give an almost quantitative yield of the titled isothiocyanate as a pale brown solid.

EXAMPLE 6

Preparation of N-(2,6-bis(trifluoromethyl)-4-pyridinyl)-N'-3,4-dichlorophenylurea 4-Isocyanato-2,6-bis(trifluoromethyl)pyridine (1.28 g, 0.005 mole) (prepared as in Example 4) in dry benzene (10 ml) was mixed with 3,4-dichloroaniline (0.81 g, 0.005 mole) in dry benzene (10 ml). The mixture was allowed to stand at ambient temperature for 2 hours and then filtered 1.4 g, m.p. 207°–209° C. Crystallization from benzene gave the titled compound as a colorless solid, m.p. 211.5°–212.5° C.

$C_{14}H_7Cl_2F_6N_3O$ Found: C, 39.97; H, 1.94; N, 9.96. Req.: C, 40.19; H, 1.67; N, 10.05%.

EXAMPLE 7

Preparation of N-(2,6-bis(trifluoromethyl)-4-pyridinyl)-N'-(4-trifluoromethylphenyl)thiourea A mixture of 4-aminobenzotrifluoride (1.48 g) and 4-isothiocyanato-2,6-bis(trifluoromethyl)pyridine (2.5 g, 0.01 mole) in dry benzene (25 ml) containing several drops of triethylamine was heated under reflux for 7 hours. Removal of the solvent and triethylamine gave the title compound as a colorless solid 2.9 g, m.p. 125°–132° C. Crystallization from benzene furnished a sample, m.p. 132° C.

$C_{15}H_8F_9N_3S$ Found: C, 41.46; H, 2.00; N, 9.97; F, 39.25. Req.: C, 41.57; H, 1.85; N, 9.70; F, 39.49%.

The following compounds were obtained by methods analogous to those employed in Examples 6 and 7.

TABLE I

| Compound | R | X | % Yield | Solvent of crystallization/ crystal form | m.p. °C. | Elemental analysis % Req./Found C | H | N |
|---|---|---|---|---|---|---|---|---|
| 1 | 2-CH₃ | O | 43 | Benzene | 260 | 49.59 / 49.45 | 3.03 / 3.45 | 11.57 / 11.13 |
| 2 | 2-Cl | S | 30 | Pet. ether | 152 | 42.05 / 42.34 | 2.00 / 2.30 | 10.51 / 10.22 |
| 3 | 2-Cl | O | 51 | Benzene/- col. needles | 204 | 43.81 / 43.83 | 2.09 / 1.99 | 10.95 / 10.93 |
| 4 | 2-CF₃ | S | 42 | Pet. ether/- col. needles | 161 | 41.57 / 41.81 | 1.85 / 2.00 | 9.70 / 10.00 |
| 5 | 2-CF₃ | O | 45 | Benzene | 211 | 43.16 / 42.90 | 1.91 / 2.00 | 10.07 / 10.14 |
| 6 | 3-CH₃ | O | 29 | Benzene/- fawn needles | 204 | 49.59 / 50.08 | 3.03 / 3.42 | 11.57 / 11.56 |
| 7 | 3-OCH₃ | O | 18 | Benzene/- fawn needles | 192 | 47.49 / 47.34 | 2.90 / 2.99 | 11.08 / 11.00 |
| 8 | 3-CN | O | 42 | Washed residue/- pale yellow needles | 277 | 48.18 / 48.36 | 2.14 / 2.18 | 14.97 / 15.07 |
| 9 | 3-Cl | O | 47 | Benzene/- col. needles | 205 | 43.81 / 44.14 | 2.09 / 2.34 | 10.95 / 10.66 |
| 10 | 3-F | O | 64 | Benzene/- fawn needles | 203 | 45.78 / 45.73 | 2.18 / 2.58 | 11.44 / 11.75 |
| 11 | 3-CF₃ | O | 46 | Benzene | 184 | 43.16 / 43.16 | 1.91 / 2.31 | 10.07 / 10.27 |
| 12 | 4-CH₃ | O | 22 | Benzene/- col. needles | 241 | 49.59 / 50.36 | 3.03 / 3.20 | 11.57 / 11.46 |
| 13 | 4-OCH₃ | S | 10 | Benzene and Pet. ether | 165 | 45.57 / 45.36 | 2.78 / 3.02 | 10.63 / 10.75 |
| 14 | 4-OCH₃ | O | 56 | Benzene/- col. needles | 202 | 47.49 / 47.19 | 2.90 / 3.25 | 11.08 / 10.99 |
| 15 | 4-CN | O | 78 | Ethyl acetate | >300 | 48.13 / 47.82 | 2.14 / 2.35 | 14.97 / 15.19 |
| 16 | 4-NO₂ | O | 35 | Ethyl acetate and benzene | >300 | 42.64 / 42.53 | 2.09 / 1.99 | 10.95 / 10.93 |
| 17 | 4-Cl | S | 42 | Benzene and Pet. ether | 125 | 42.05 / 42.21 | 2.00 / 2.05 | 10.51 / 10.91 |
| 18 | 4-Cl | O | 45 | Benzene/- col. needles | 204 | 43.81 / 44.43 | 2.09 / 2.29 | 10.95 / 10.76 |
| 19 | 4-CF₃ | S | 67 | Benzene | 132 | 41.57 / 41.46 | 1.85 / 2.00 | 9.70 / 9.97 |

TABLE I-continued

| Compound | R | X | % Yield | Solvent of crystallization/ crystal form | m.p. °C. | Elemental analysis % Req./Found | | |
|---|---|---|---|---|---|---|---|---|
| | | | | | | C | H | N |
| 20 | 4-$CF_3$ | O | 76 | Benzene/- col. prisms | 199 | 43.17 42.91 | 1.92 2.08 | 10.07 10.14 |
| 21 | 2,3-$Cl_2$ | O | 64 | Benzene/- fawn needles | 212 | 40.19 40.54 | 1.67 1.79 | 10.05 9.60 |
| 22 | 2,4-$Cl_2$ | O | 51 | Benzene/- col. needles | 199 | 40.19 40.75 | 1.67 1.58 | 10.05 9.68 |
| 23 | 2,5-$Cl_2$ | O | 57 | Benzene/- col. needles | 199 | 40.19 40.56 | 1.67 1.72 | 10.05 9.84 |
| 24 | 2,6-$Cl_2$ | O | 33 | Benzene/- col. needles | 230 | 40.19 40.36 | 1.67 1.86 | 10.05 10.23 |
| 25 | 3,4-$Cl_2$ | O | 67 | Benzene/- col. flakes | 212 | 40.19 39.97 | 1.67 1.94 | 10.05 9.96 |
| 26 | 2,4,5-$Cl_3$ | O | 30 | Benzene/- col. needles | 223 | 37.13 37.46 | 1.33 1.31 | 9.28 9.54 |
| 27 | 2,4,6-$Cl_3$ | O | 38 | Benzene/- col. needles | 243 | 37.13 37.26 | 1.33 1.18 | 9.28 9.41 |
| 28 | 3,4,5-$Cl_3$ | O | 69 | Benzene/- col. needles | 239 | | | 9.28 8.82 |
| 29 | $Cl_5$ | O | 26 | Benzene/- col. needles | 295 | 32.21 32.44 | 0.77 0.68 | 8.05 8.04 |
| 30 | 4-Cl,3-$CF_3$ | O | 64 | Benzene/- col. needles | 177 | | | 9.30 8.85 |
| 31 | 4-SCN,3-Cl | O | 69 | Benzene and ethanol/fawn needles | 217 | | | 12.71 12.12 |
| 32 | 3,5($CF_3$)$_2$ | O | 20 | Benzene/- col. needles | 192 | | | 8.59 8.70 |

The active compounds according to the invention exhibit a strong fungitoxic action. Their low toxicity to mammals and their good tolerance by higher plants is advantageous in their use as plant protection agents. Compositions containing these compounds may be applied to growing vegetation in amounts required for effective control without significant injury to the plants.

It has been found that the present compounds are particularly adapted to be employed for the control of a wide range of bacteria and fungi from the most diverse classes such as Oomycetes, Ascomycetes, Basidiomycetes and Fungi Imperfecti. The active compounds according to the invention, can be used against parasitic fungi on above ground parts of plants, fungi which attack the plant through the soil, seed-borne fungi and fungi which inhabit the soil. They are particularly active against Ascomycetes, Oomycetes and Fungi Imperfecti. The following may be mentioned as important fungi to be combated with the above active compounds according to the invention: *Plasmopara viticola, Erysiphe graminis, Podosphaera leucotricha* and *Phytophthara parasitica* var *nicotinae*.

In other operations, the compounds can be included in inks, adhesives, soaps, cutting oils, polymeric materials, or in oil or latex paints, to prevent mold, mildew, and the degradation of such products resulting from microbial attack. Also the compounds can be distributed in textile or cellulosic materials, or can be employed in the impregnation of wood and lumber to preserve and protect such products from the attack of the microbial agents of rot, mold, mildew and decay. The foregoing environments are merely illustrative of the many habitats in which these agents can be distributed to obtain excellent fungal control.

The method of the present invention comprises contacting a fungal organism with a fungicidal amount of one or more of the compounds. However, the present invention also embraces the employment of a liquid, powder or dust composition containing one or more of the compounds and one or more additives including organic solvents, petroleum distillates, water or other liquid carriers, surface active dispersing agents, and finely divided inert solids. In such compositions, the compounds oftentimes are present in a concentration from 2 to 98 percent by weight or when the carrier is a surface active agent, from 0.1 to 20 percent by weight. Depending upon the concentration in the composition of the compound, such augmented compositions are adapted to be employed for the control of the undesirable fungi or employed as concentrates and subsequently diluted with additional inert carrier to produce the ultimate treating compositions. In general, however, good results can be obtained with liquid compositions containing from 0.0001 to 2.0 percent by weight of the toxicant. With dusts, good results can usually be obtained with compositions containing from 0.0001 to 2.0 percent or more by weight of toxicant. Where the compositions are to be applied to living plants, it is preferred that the toxicant be present in an amount not to exceed 0.8 percent in liquid compositions and 1.0 percent in dusts. In terms of acreage application, good controls of fungal organisms can be obtained when the compounds are applied to plots of growing plants at a dosage of from 0.004 to 3 or more pounds per acre (0.0045 to 3.36 kg/hectare).

In the protection and preservation of inks, adhesives, cutting oils, paints, textiles and paper, good results can be obtained when the compounds are incorporated in such products in the amount of at least 0.0001 percent by weight. In the preservation of wood, excellent results can be obtained when the compounds are incorporated by conventional treatment in the wood in the amount of at least 0.0001 pound per cubic foot (0.0016 kg/cu.m) of wood.

The fungicidal and bactericidal activity of the compounds of the present invention are illustrated by the following examples where solutions or suspensions of the test chemical were prepared, at the desired concentration, in aqueous acetone or isopropanol containing a small amount of a suitable wetter.

EXAMPLE 8

Grape downy mildew protectant test

The underside of the leaves of grape seedlings (cv. Carignane) at the 3-4 leaf stage were sprayed with an aqueous suspension of the test material. After application, the underside of the plant leaves were sprayed with a spore suspension of *Plasmopara viticola* in distilled water. The plants were held in an infection chamber at 20° to 22° C. and 100% r.h. for 7-8 days. When the disease symptoms were well developed, the seedlings were graded for disease control by rating seedlings, treated with the above solution (suspension) less toxicants, as 'no control' and treated plants with the absence of disease symptoms as '100% control'.

The active compounds, their concentration of use and the results can be seen from the following table.

TABLE II

| Active Compound Number | Grape Downy Mildew/Protectant Control in % over an active compound concentration range of | | | |
|---|---|---|---|---|
| | 0.04% | 0.01% | 0.0025% | 0.00062% |
| 2 | 100 | 70 | 35 | — |
| 3 | 100 | 100 | 70 | — |
| 4 | 100 | 75 | 25 | — |
| 6 | 75 | — | — | — |
| 7 | 85 | 75 | 35 | — |
| 8 | 83 | — | — | — |
| 9 | 85 | 45 | 5 | — |
| 10 | 90 | 50 | 30 | — |
| 11 | 100 | 90 | 55 | — |
| 12 | 100 | 85 | 75 | — |
| 13 | — | 100 | — | — |
| 14 | 100 | 40 | 5 | — |
| 15 | 80 | 45 | 25 | — |
| 16 | 100 | 30 | 0 | — |
| 17 | 100 | 70 | 25 | — |
| 18 | 100 | 100 | 40 | — |
| 19 | — | 99 | — | — |
| 20 | 95 | 90 | 90 | — |
| 21 | 50 | — | — | — |
| 22 | 100 | 100 | 0 | — |
| 23 | 50 | — | — | — |
| 25 | — | — | 99 | 50 |
| 26 | 40 | — | — | — |
| 28 | — | 100 | 100 | 67 |
| 29 | 75 | — | — | — |
| 30 | 100 | 100 | 93 | 50 |
| 32 | — | 25 | — | — |

EXAMPLE 9

Cereal powdery mildew protectant test

Barley plants (cv. BERAC) at the 1-2 leaf stage were sprayed with an aqueous suspension of the test chemical by a moving nozzle sprayer until just completely wet. The plants were allowed to stand and dry (3-4 hours) and then inoculated by dry dusting with conidia of *Erysiphe graminis* before being placed in a greenhouse at 20°-25° C. with a minimum day length of 12 hours. Assessment was made 7-8 days later, where plants, treated with the above solution (suspension) less toxicants, were rated as 'no control' and treated plants with the absence of disease symptoms as '100% control'.

The active compounds, their concentration of use and the results can be seen from the following table.

TABLE III

| Active Compound Number | Cereal Powdery Mildew/Protectant Control in % over an active compound concentration range of | | |
|---|---|---|---|
| | 0.04% | 0.01% | 0.0025% |
| 1 | 65 | 56 | 42 |
| 3 | 47 | 28 | 26 |
| 7 | 58 | 40 | 14 |
| 8 | 54 | 42 | 19 |
| 9 | 46 | 28 | 23 |
| 12 | 44 | 37 | 33 |
| 14 | 49 | 42 | 38 |
| 15 | 44 | 33 | 26 |
| 16 | 54 | 35 | 12 |
| 20 | 44 | 37 | 30 |
| 21 | 47 | 44 | 29 |
| 22 | 53 | 47 | 29 |
| 23 | 60 | 47 | 20 |
| 24 | 53 | 53 | 29 |
| 25 | 44 | 36 | 24 |
| 26 | 49 | 33 | 16 |
| 27 | 53 | 42 | 20 |
| 29 | 67 | 53 | 31 |

EXAMPLE 10

Apple powdery mildew protectant test

Apple seedlings (cv. Red Delicious) at the 4-6 leaf stage were sprayed to run off with a solution or suspension of the test chemical. The plants were held in a greenhouse for 48 hours at 20°-22° C. and then inoculated with an aqueous suspension of freshly harvested conidia of *Podosphaera leucotricha* ($10^6$ propagules/ml). The plants were graded after 7-12 days when inoculated, but untreated, plants sporulated profusely. The assessments were expressed as a percent control where inoculated plants treated with the above solutions (suspension) less toxicant were rated as 'no control' and treated plants with the absence of disease symptoms as '100% control'.

The active compounds, their concentrations of use and the results can be seen from the following table.

TABLE IV

| Active Compound Number | Apple Powdery Mildew/Protectant Control in % at an active compound concentration of 0.04% |
|---|---|
| 19 | 50 |
| 25 | 90 |
| 28 | 95 |
| 30 | 100 |
| 32 | 90 |

EXAMPLE 11

Tobacco black shank root drench test

Tobacco seedlings (cv. Coker) at the third leaf stage were transplanted into soil heavily infested with *Phytophthora parasitica* var *nicotinae*. The soil was drenched with the toxicant solution on suspension (30 ml) at the appropriate concentration and the plants then incubated above soil beds heated to 29° C. to enhance disease development. The test was graded on the basis of transplant survival and expressed as a percent: 0% means no plants survived; 100% means that the test was equivalent to an uninoculated control.

The active compounds, their concentrations of use and the results can be seen from the following table.

TABLE V

Tobacco Black Shank/Root Drench

| Active Compound Number | Control in % at an active compound concentration of 0.0025% |
|---|---|
| 10 | 100 |
| 11 | 100 |
| 14 | 100 |
| 17 | 100 |

EXAMPLE 12

Anti-fungal and anti-bacterial 'in vitro' tests

The test compounds were applied as solutions or suspensions in isopropanol to warm melted agar to achieve the desired concentration and then poured into petri dishes and allowed to solidify. Droplets of the appropriate test organism were applied to the surface of the agar with an 'Accu Drop'. The plates were incubated at the appropriate temperature and time for the organism. The tests were assessed for inhibition of 50% of the organism and the IC$_{50}$ recorded as the lowest concentration at which this was achieved. The active compounds and the results can be seen from the following table.

TABLE VI

| Active Compound Number | Control expressed as an IC$_{50}$ μg/ml on the following organisms | | | | | |
|---|---|---|---|---|---|---|
| | S.m. | S.a. | T.m. | B.s. | C.p. | P.p. | R.n. |
| 18 | | 1.0 | 1.0 | 10.0 | 10.0 | 10.0 | 10.0 |
| 19 | 0.06 | 0.5 | 5.0 | 1.0 | 50.0 | 10.0 | |
| 25 | | 1.0 | 1.0 | 1.0 | | 1.0 | 1.0 |
| 28 | | 1.0 | 1.0 | 1.0 | | 1.0 | 1.0 |
| 30 | | 1.0 | 1.0 | 1.0 | | 1.0 | 1.0 |
| 31 | | 1.0 | | 1.0 | | | 10.0 |

S.m., *Streptococcus mutans*;
S.a., *Staphylococcus aureus*;
T.m., *Tricophton mentagrophytes*;
B.s., *Bacillus subtillis*;
C.p., *Candida pelliculosa*;
P.p., *Pullularia pullulans*;
R.n., *Rhizopus nigricans*.

What is claimed is:

1. A compound corresponding to the formula

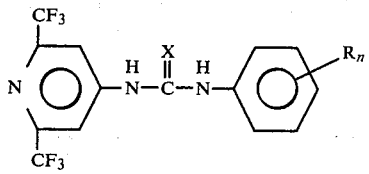

wherein R is halogen, trichloromethyl, trifluoromethyl, nitro, cyano, C$_1$–C$_4$ alkyl or C$_1$–C$_4$ alkoxy; X is O or S and n is an integer of from 1 to 5.

2. The compound of claim 1 wherein X is O or S, R is 4-CF$_3$; 3,4-Cl$_2$; 3-CF$_3$,4-Cl; 3,4,5-Cl$_3$; 3-CF$_3$; 4-Cl; or 4-OCH$_3$.

3. The compound of claim 2 which is N-(2,6-bis(trifluoromethyl)-4-pyridinyl)-N'-(3,4-dichlorophenyl)thiourea.

4. The compound of claim 2 which is N-(2,6-bis(trifluoromethyl)-4-pyridinyl)-N'-(4-methoxyphenyl)thiourea.

5. The compound of claim 2 which is N-(2,6-bis(trifluoromethyl)-4-pyridinyl)-N'-(4-chlorophenyl)thiourea.

6. The compound of claim 2 which is N-(2,6-bis(trifluoromethyl)-4-pyridinyl)-N'-(4-trifluoromethylphenyl)thiourea.

7. A fungicidal or bactericidal composition comprising as the active fungicide or bactericide, a fungicidally and bactericidally effective amount of a compound corresponding to the formula

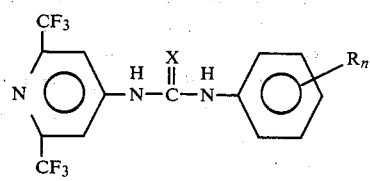

wherein R is halogen, trichloromethyl, trifluoromethyl, nitro, cyano, C$_1$–C$_4$ alkyl or C$_1$–C$_4$ alkoxy; X is O or S and n is an integer of from 1 to 5 in intimate admixture with an inert carrier therefor.

8. The composition of claim 7 wherein X is O or S; R is 4-CF$_3$; 3,4-Cl$_2$; 3-CF$_3$,4-Cl; 3,4,5-Cl$_3$; 3-CF$_3$; 4-Cl; or 4-OCH$_3$.

9. The composition of claim 8 wherein the compound is N-(2,6-bis(trifluoromethyl)-4-pyridinyl)-N'-(3,4-dichlorophenyl)thiourea.

10. The composition of claim 8 wherein the compound is N-(2,6-bis(trifluoromethyl)-4-pyridinyl)-N'-(4-methoxyphenyl)thiourea.

11. A method of controlling fungal or bacterial organisms, which method comprises contacting the organisms with a fungicidally or bactericidally effective amount of a composition comprising an inert carrier in intimate admixture with a compound corresponding to the formula

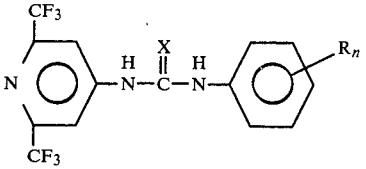

wherein R is halogen, trichloromethyl, trifluoromethyl, nitro, cyano, C$_1$–C$_4$ alkyl or C$_1$–C$_4$ alkoxy; X is O or S and n is an integer of from 1 to 5.

12. The method of claim 11 wherein X is O or S; R is 4-CF$_3$; 3,4-Cl$_2$; 3-CF$_3$,4-Cl; 3,4,5-Cl$_3$; 3-CF$_3$; 4-Cl; or 4-OCH$_3$.

13. The method of claim 12 wherein the compound is N-(2,6-bis(trifluoromethyl)-4-pyridinyl)-N'-(3,4-dichlorophenyl)thiourea.

14. The method of claim 12 wherein the compound is N-(2,6-bis(trifluoromethyl)-4-pyridinyl)-N'-(4-methoxyphenyl)thiourea.

* * * * *